United States Patent
Gliner et al.

(10) Patent No.: US 11,646,113 B2
(45) Date of Patent: May 9, 2023

(54) SYSTEMS AND METHODS FOR DETERMINING MAGNETIC LOCATION OF WIRELESS TOOLS

(71) Applicant: Biosense Webster (Israel) Ltd., Yokneam (IL)

(72) Inventors: Vadim Gliner, Haifa (IL); Yaron Ephrath, Karkur (IL)

(73) Assignee: Biosense Webster (Israel) Ltd., Vokneam (IL)

( * ) Notice: Subject to any disclaimer, the term of this patent is extended or adjusted under 35 U.S.C. 154(b) by 272 days.

(21) Appl. No.: 15/935,777

(22) Filed: Mar. 26, 2018

(65) Prior Publication Data

US 2018/0308577 A1 Oct. 25, 2018

Related U.S. Application Data

(60) Provisional application No. 62/489,019, filed on Apr. 24, 2017.

(51) Int. Cl.
*A61B 34/00* (2016.01)
*G16H 40/60* (2018.01)
(Continued)

(52) U.S. Cl.
CPC ............ *G16H 40/60* (2018.01); *A61B 5/062* (2013.01); *A61B 5/067* (2013.01); *A61B 34/20* (2016.02);
(Continued)

(58) Field of Classification Search
CPC .. G16H 40/60; A61B 5/067; A61B 2034/2048
See application file for complete search history.

(56) References Cited

U.S. PATENT DOCUMENTS

| 5,391,199 | A | 2/1995 | Ben-Haim |
| 5,443,489 | A | 8/1995 | Ben-Haim |

(Continued)

FOREIGN PATENT DOCUMENTS

| EP | 1096268 A2 | 5/2001 |
| EP | 2632381 A1 | 9/2013 |

(Continued)

OTHER PUBLICATIONS

Furuno, "Technology Dead Reckoning (DR)," Dec. 4, 2014 [retrieved on Mar. 6, 2020]. Retrieved from the Internet: <URL:https://web.archive.org/web/20141204081651/https://www.furuno.com/en/gnss/technical/tec_dead>. (Year: 2014).*

(Continued)

*Primary Examiner* — Mohamed Charioui
*Assistant Examiner* — Christine Y Liao
(74) *Attorney, Agent, or Firm* — Volpe Koenig (57) ABSTRACT

A method for locating a tool in a 3D space is provided. The method includes determining whether location data, corresponding to a location of the tool, is available. If the location data is available, the method includes providing the location data for presenting the location of the tool. If the location data is not available, the method includes determining an estimated location of the tool based on a velocity of the tool and an acceleration of the tool, generating estimated location data corresponding to the estimated location of the tool and providing the estimated location data for presenting the estimated location as the location of the tool. The method also includes determining whether accelerometer data is available. If accelerometer data is available, the method includes using the accelerometer data to estimate the location of the tool.

20 Claims, 4 Drawing Sheets

(51) Int. Cl.
*A61B 34/20* (2016.01)
*A61B 5/06* (2006.01)

(52) U.S. Cl.
CPC ............ *A61B 2034/2048* (2016.02); *A61B 2034/2051* (2016.02); *A61B 2034/2065* (2016.02)

(56) References Cited

U.S. PATENT DOCUMENTS

| | | | |
|---|---|---|---|
| 5,558,091 A | 9/1996 | Acker et al. | |
| 6,172,499 B1 | 1/2001 | Ashe | |
| 6,177,792 B1 | 1/2001 | Govari et al. | |
| 6,266,551 B1 | 7/2001 | Osadchy et al. | |
| 6,611,141 B1 | 8/2003 | Schulz et al. | |
| 6,690,963 B2 | 2/2004 | Ben-Haim et al. | |
| 6,788,967 B2 | 9/2004 | Ben-Haim et al. | |
| 8,457,880 B1* | 6/2013 | Malalur | G01C 21/30 701/410 |
| 9,791,279 B1* | 10/2017 | Somieski | G01C 21/165 |
| 2002/0049375 A1* | 4/2002 | Strommer | A61B 5/0066 600/407 |
| 2003/0078509 A1* | 4/2003 | Panescu | A61B 5/063 600/509 |
| 2006/0287824 A1* | 12/2006 | Lin | G01C 21/165 701/472 |
| 2007/0197905 A1 | 8/2007 | Timinger et al. | |
| 2007/0270686 A1* | 11/2007 | Ritter | A61B 5/06 600/424 |
| 2009/0009398 A1* | 1/2009 | Taylor | G01S 5/0072 342/451 |
| 2009/0082660 A1* | 3/2009 | Rahn | A61B 6/12 600/411 |
| 2009/0143677 A1* | 6/2009 | Govari | A61B 8/5238 600/439 |
| 2009/0149740 A1 | 6/2009 | Hoheisel | |
| 2011/0071759 A1* | 3/2011 | Pande | G01C 21/165 701/469 |
| 2011/0125150 A1* | 5/2011 | Deno | A61B 5/743 606/34 |
| 2012/0232377 A1* | 9/2012 | Nottmeier | A61B 34/20 600/411 |
| 2013/0103064 A1* | 4/2013 | Arenson | A61N 7/022 606/169 |
| 2014/0039748 A1* | 2/2014 | Friend | G06F 11/30 701/29.7 |
| 2014/0051968 A1* | 2/2014 | Isham | A61N 5/10 600/407 |
| 2014/0128739 A1 | 5/2014 | Sundaran et al. | |
| 2014/0187905 A1 | 7/2014 | Olson | |
| 2014/0243641 A1* | 8/2014 | Boveja | A61B 5/0035 600/374 |
| 2015/0120207 A1* | 4/2015 | Yang | A61B 5/316 702/19 |
| 2015/0223757 A1* | 8/2015 | Werneth | A61B 8/4494 600/301 |
| 2015/0305823 A1 | 10/2015 | Claus | |
| 2016/0096003 A1* | 4/2016 | Parmar | A61M 25/0111 604/510 |
| 2016/0106336 A1* | 4/2016 | Li | A61B 5/0536 600/374 |
| 2016/0146616 A1* | 5/2016 | Ren | G01C 21/30 701/409 |
| 2016/0278652 A1* | 9/2016 | Kaib | G16H 50/20 |
| 2016/0324485 A1* | 11/2016 | Erdemir | A61B 5/339 |
| 2016/0354158 A1* | 12/2016 | Razavi | A61B 5/318 |
| 2017/0055940 A1* | 3/2017 | Shoham | A61B 8/0841 |
| 2017/0065348 A1* | 3/2017 | Fish | A61B 34/10 |
| 2017/0157361 A1* | 6/2017 | Barrish | A61B 34/20 |
| 2018/0153505 A1* | 6/2018 | Cadieu | A61B 8/4254 |
| 2019/0000339 A1* | 1/2019 | Kessman | G16H 20/30 |

FOREIGN PATENT DOCUMENTS

| | | |
|---|---|---|
| JP | 2002-533721 A | 10/2002 |
| WO | 2012/057871 A1 | 5/2012 |

OTHER PUBLICATIONS

Pless et al., "u-blox 3D Dead Reckoning for Vehicle Applications," Jan. 2014, u-blox AG (Year: 2014).*
Extended European Search Report dated Sep. 13, 2018 for the European Patent Application No. 18168987.8.
Japanese Office Action dated Mar. 23, 2022 for Japanese Patent Application No. 2018-082063.

* cited by examiner

SYSTEMS AND METHODS FOR DETERMINING MAGNETIC LOCATION OF WIRELESS TOOLS

CROSS-REFERENCES TO RELATED APPLICATIONS

This application claims priority to U.S. Provisional Patent Application No. 62/489,019, filed on Apr. 24, 2017, which is incorporated herein by reference.

SUMMARY

A method for locating a tool in a three dimensional (3D) space is provided. The method includes determining whether location data, corresponding to a location of the tool, is available. If the location data is available, the method includes providing the location data for presenting the location of the tool. If the location data is not available, the method includes determining an estimated location of the tool based on a velocity of the tool and an acceleration of the tool, generating estimated location data corresponding to the estimated location of the tool and providing the estimated location data for presenting the estimated location as the location of the tool. The method also includes determining whether accelerometer data is available. If accelerometer data is available, the method includes using the accelerometer data to estimate the location of the tool.

An electromagnetic navigation system for locating a tool in a 3D space is provided. The system includes memory configured to store data and a processor, in communication with the memory. The processor is configured to determine whether location data, corresponding to a location of the tool, is available. If the location data is available, the processor is configured to provide the location data for presenting the location of the tool. If the location data is not available, the processor is configured to determine an estimated location of the tool based on a velocity of the tool and an acceleration of the tool, generate estimated location data corresponding to the estimated location of the tool and provide the estimated location data for presenting the estimated location as the location of the tool.

A non-transitory computer readable medium is provided. The computer readable medium has instructions which when executed cause a computer to perform a method of locating a tool in a 3D space. The method includes determining whether location data, corresponding to a location of the tool, is available. If the location data is available, the method includes providing the location data for presenting the location of the tool. If the location data is not available, the method includes determining an estimated location of the tool based on a velocity of the tool and an acceleration of the tool, generating estimated location data corresponding to the estimated location of the tool and providing the estimated location data for presenting the estimated location as the location of the tool. The method also includes determining whether accelerometer data is available. If accelerometer data is available, the method includes using the accelerometer data to estimate the location of the tool.

BRIEF DESCRIPTION OF THE DRAWINGS

A more detailed understanding can be had from the following description, given by way of example in conjunction with the accompanying drawings wherein.

DETAILED DESCRIPTION

Electromagnetic navigation systems are used to determine the location of medical tools in a 3-D space during a medical procedure. During the procedures, medical tools generate and transmit signals (e.g., electrical signals based on the amplitude and phase of magnetic fields) to facilitate the determination of their locations. In some conventional systems, the signals are transmitted to system components via a wired medium (e.g., cable).

Due to the advancement in short-range radio technology, however, some systems utilize tools that are wirelessly connected to the system components and the signals are wirelessly transmitted to the system components via various short range wireless protocols (Institute of Electrical Engineers (IEEE) 802.11g IrDA (infrared data) and Ericsson Bluetooth™. For example, medical personnel (e.g., ear, nose and throat (ENT) physicians and cardiologists) use battery-powered tools, such as catheters, for performing the medical procedures on patient anatomy. Based on the determined locations of the tools, anatomical information of a patient is presented (e.g., displayed) to the medical personnel. Accordingly, the efficiency and success of the procedures rely on continually providing the locations of the tools.

The present application discloses systems, apparatuses and methods of using magnetic fields to calculate the location of medical tools in a 3-D space. Each tool is configured to wirelessly send data (e.g., location data using the magnetic fields (hereinafter "location data"), velocity data and acceleration data) to a processing device for mapping the location of the tool in the 3-D space. When the location data, corresponding to the location of the tool in the 3-D space at a point in time or time period, is not available (e.g., the location data is not received at the processing device, the data is inaccurate) for processing, the processing device uses previously calculated data to estimate the tool's location in a 3-D space. For example, the processing device uses previously calculated data corresponding to the tool's velocity and acceleration at different locations over time. The velocity and acceleration of the tool may be continually calculated during operation such that calculated data is available for processing to estimate the location of the tool when the location data is not available for processing. The processing device may also determine whether accelerometer data (i.e., acceleration data from an accelerometer at the tool) is available for processing and use the accelerometer data, in addition to or alternative to the previously calculated data, to estimate the tool's location in the 3-D space.

Figure 1:
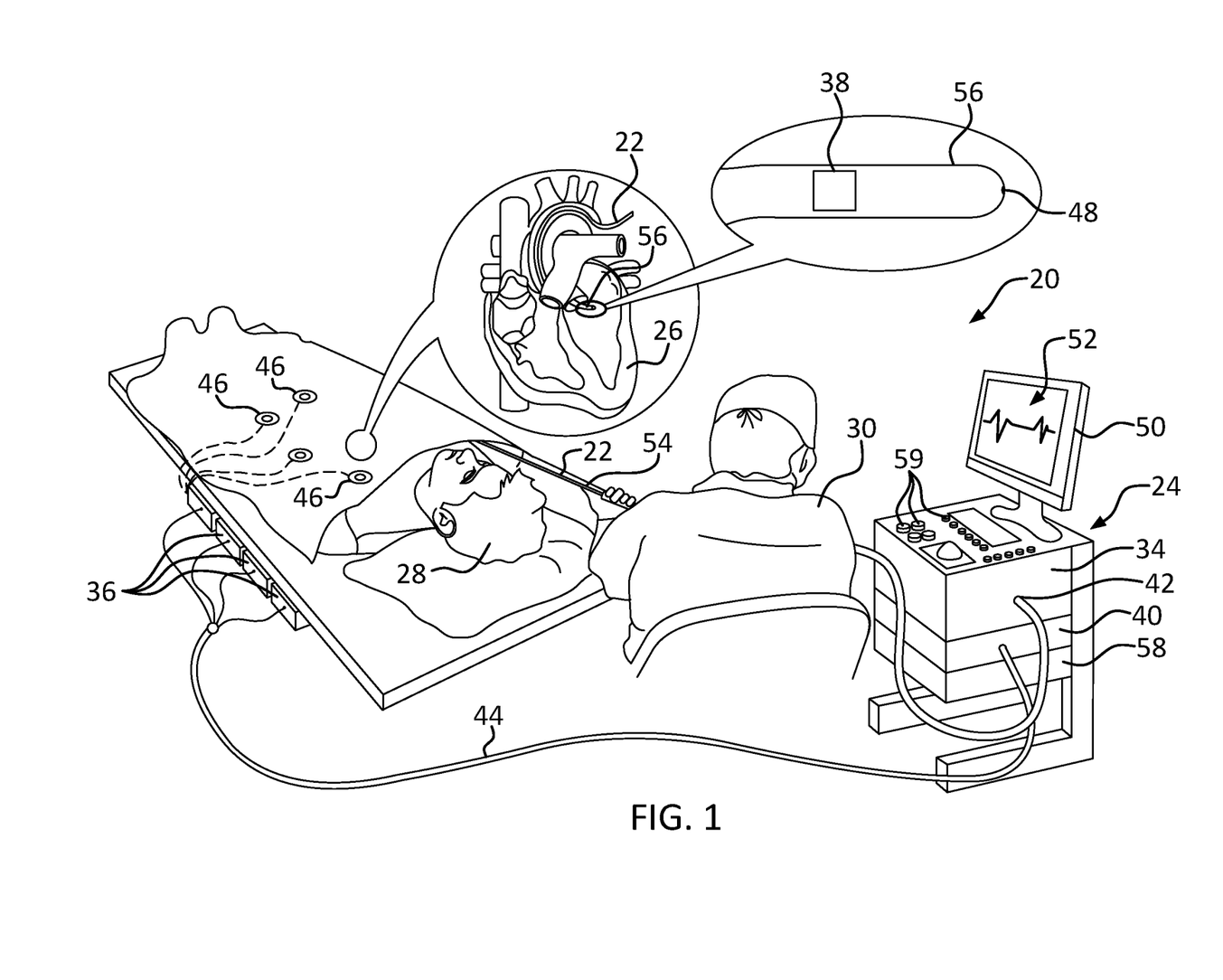
FIG. 1 is an illustration of an example medical system for navigating a tool in a 3-D space within which embodiments disclosed herein may be implemented.

Referring now to FIG. 1, an illustration of an example medical system 20 is shown that may be used to generate and display information 52 (e.g., a chart, anatomical models of a portion of a patient and signal information). The system 20 and the tool 22 shown in FIG. 1 are merely by example. Medical tools, such as tool 22, can be any tool used for diagnostic or therapeutic treatment, such as for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22, which may include a non-tip section 54 and a tip 56 into a portion of patient anatomy, such as the vascular system of the patient 28 so that the tip 56 of the tool 22 enters a chamber of the heart 26. The control console 24 may use magnetic position sensing to determine position coordinates of the tool 22 (e.g., coordinates of the tip 56) in 3-D space inside the heart 26. To determine the position coordinates, a driver circuit 34 in the control console 24 may drive, via connector 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils is driven by a different frequency to emit a constant magnetic field in 3-D space. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 is used to determine the position of the receiving coil in 3-D space and generate electrical signals based on the amplitude and phase of the magnetic fields. Although the magnetic field location sensor 38 is disposed at the tip 56 of tool 22, a tool can include one or more magnetic field location sensors each disposed at any portion of the tool.

The signals are wirelessly communicated to the control console 24 via a wireless communication interface at the tool 22 that may communicate with a corresponding input/output (I/O) interface 42 in the control console 24. The wireless communication interface and the I/O interface 42 may operate in accordance with any suitable wireless communication standard that is known in the art, such as for example, infrared (IR), radio frequency (RF), Bluetooth, one of the IEEE 802.11 family of standards (e.g., Wi-Fi), or the HiperLAN standard. The body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery, as described in more detail below.

The I/O interface 42 may enable the control console 24 to interact with the tool 22, the body surface electrodes 46 and the position sensors (not shown). Based on the electrical impulses received from the body surface electrodes 46 and the electrical signals received from the tool 22 via the I/O interface 42 and other components of medical system 20, the processor 40 may determine the location of the tool in 3-D space and generate the display information 52, which may be shown on a display 50. Although display information 52 is shown on a display 50, it is possible to generate and present the location of the tool 22 in any known manner such as audibly.

Processor 40, which may include one or more processors, is configured to process the signals (e.g. process information contained in signal packets) to determine the position coordinates of the tip 56 in 3-D space, including both location and orientation coordinates. The location data can include points in 3-D space, strength of the magnetic field and a time stamp. The processor 40 may be also used to implement any portion of the methods for locating a tool in a 3D space described herein, such as determining the availability of location data and accelerometer data, determining the location of the tool 22 based on the location data, estimating the location of the tool 22 based on accelerometer data and previously calculated data (e.g., velocity and acceleration data), filtering (e.g., via a Kalman filter) estimated location data and generating the display information 52, which may be shown on a display 50.

The method of position sensing described hereinabove is implemented in the CARTO mapping system produced by Biosense Webster Inc., of Diamond Bar, Calif., and is described in detail in the patents and the patent applications cited herein.

The magnetic field location sensor 38 transmits a signal to the control console 24 which indicates the location data of the tool 22 (e.g., location coordinates of the tip 56) in 3-D space. The magnetic field location sensor 38 may include one or more miniature receiving coils and may include multiple miniature coils oriented along different axes. Alternatively, the magnetic field location sensor 38 may include another type of magnetic sensor or position transducers of other types, such as impedance-based or ultrasonic location sensors. Although FIG. 1 shows the tool 22 having a single location sensor, embodiments may include tools with more than one location sensor. Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

The processor 40 may be included in a general-purpose computer, with a suitable front end and interface circuits for receiving signals from the tool 22 and controlling the other components of the control console 24. The processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28.

Additionally or alternatively, the tool 22, the body surface electrodes 46 and other sensors (not shown) may communicate with the control console 24 and one another via a wireless interface. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions.

During the diagnostic treatment, the processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is exemplary. Any suitable configuration of the medical system 20 may be used and implemented.

Figure 2:
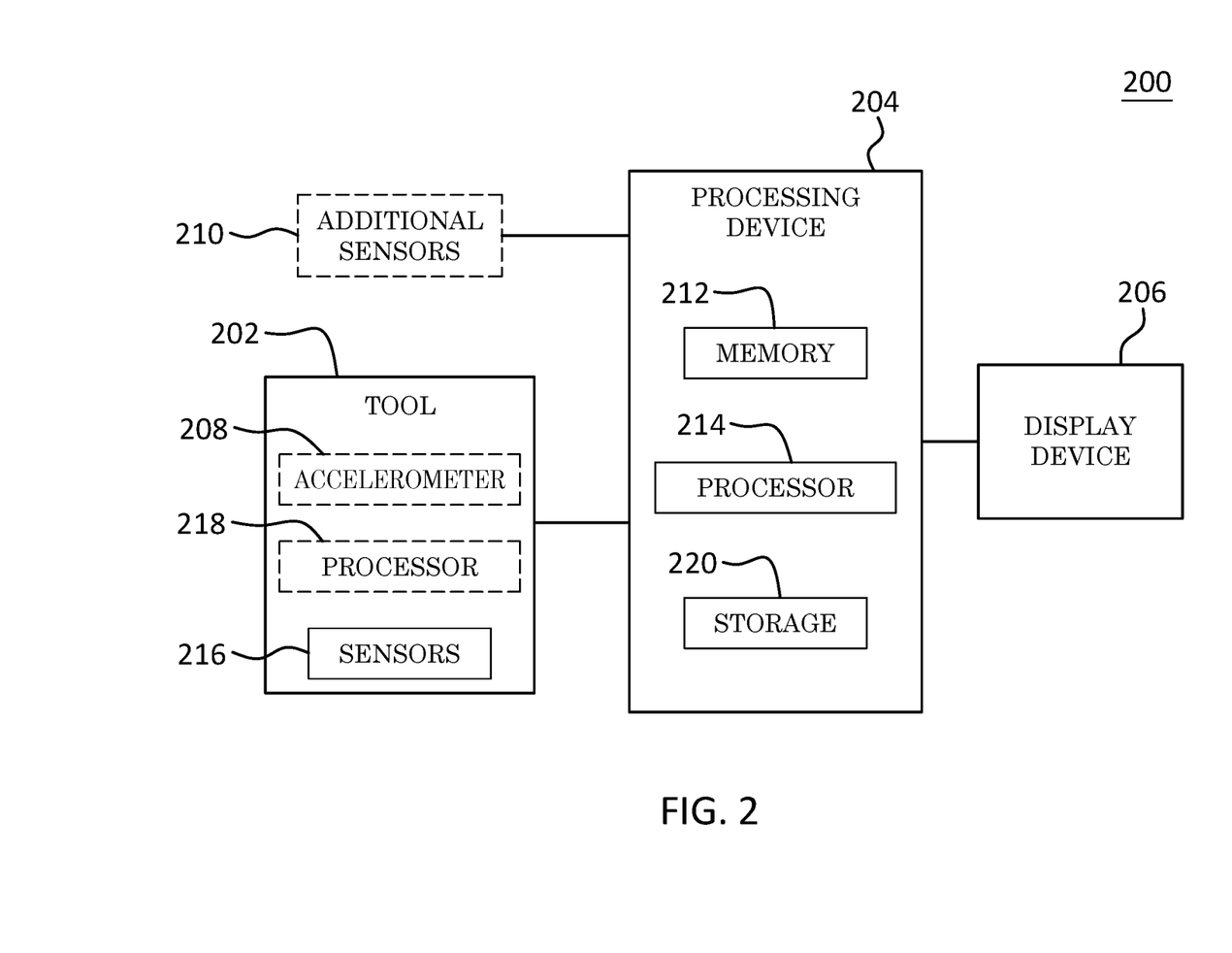
FIG. 2 is a block diagram illustrating components of an example medical system for use with embodiments described herein.

FIG. 2 is a block diagram illustrating example components of an example medical system 200 in which features described herein can be implemented. As shown in FIG. 2, the system 200 includes tool 202, processing device 204 and display device 206. The display device 206 (e.g., display 50 in FIG. 1) may be in wired communication, wireless communication or a combination of wired and wireless communication, via one or more networks (e.g., the Internet, a local area network (LAN), or a wide area network (WAN)) with processing device 204. Display device 206 may include one or more displays each configured to display different information, such as the location of the tool over time and maps of patient anatomy (e.g., map of a patient heart).

As shown in FIG. 2, processing device 204 includes processor 214, memory 212 (e.g., for storing information and instructions to be executed by processor 214) and storage 220 (e.g., a hard disk or a removable media drive). The processing device 204 and display device 206 may, for example, be part of the exemplary control console 24 shown in FIG. 1.

As shown in FIG. 2, tool 202 includes sensors 216. Sensors 216 may include one or more sensors (e.g., magnetic field location sensor 38 shown in FIG. 1 or sensors 316 shown in FIG. 3) for providing location signals to indicate the location of the tool 202 in 3-D space. As shown in FIG. 2, the system 200 may also include additional sensors 210. The additional sensors 210, which may include one or more sensors separate from the tool 202, such as surface electrodes 46 as shown in FIG. 1, for providing location signals indicating the location of the tool 202 in 3-D sp ace.

As shown in FIG. 2, processing device 204 includes processor 214, which may include one or more processors.

Processor 214 may process electromagnetic signals, record electromagnetic signals over time, filter electromagnetic signals, and generate and combine electromagnetic signal information, provide information for display and control display device 206 for displaying information on display device 206. Processor 214 may generate and interpolate mapping information for displaying maps of the heart on display device 206. Processor 214 may process the location information acquired from one or more sensors (e.g., one or more additional sensors 210 and one or more tool sensors 216) to determine location and orientation coordinates of the tool 202 (e.g., a tip portion of the tool).

Processor 214, which is in communication with memory 212, may be used to implement any portion of the methods for locating a tool in a 3D space described herein. For example, processor 214 may calculate the velocity and acceleration data based on signals acquired via sensors 216 and estimate location data based on the velocity and acceleration data. In addition, processor 214 may determine whether location data, obtained at the tool 202, which corresponds to a location of the tool 202, is available for processing. If the location data is available, processor 214 provides the location data for displaying the location of the tool 202. If the location data is not available, processor 214 estimated location data, corresponding to an estimated location of the tool 202, based on the calculated velocity and an acceleration of the tool 202, and provides (e.g., to a display processor or to the display device 206) the estimated location data for displaying the location of the tool 202 according to the estimated location. Processor 214 may also drive display device 206 to display the location of the tool 202.

In some embodiments, tool 202 may include an accelerometer 208, which is shown in phantom in FIG. 2, for detecting the acceleration of the tool 202 over time. In some embodiments, tool 202 may also include a processor 218, which is also shown in phantom in FIG. 2.

Processor 218 may be used to perform one or more functions that are performed by processor 214. For example, processor 218 may be used to calculate the velocity and acceleration data of the tool 202 based on signals acquired via sensors 216. The calculated velocity and acceleration data may then be transmitted to the processing device 204. The processing device 204 may then determine the estimated location based on the velocity and acceleration data calculated by processor 218 at the tool 202. Processor 218 may also be used to generate estimated location data, corresponding to an estimated location of the tool 202 based on the calculated velocity and acceleration data, and transmit the estimated location data to the processing device 204. The velocity and acceleration data and the estimated location data can be transmitted from the tool 202 to processor 214 using any of a number of short range wireless transmission protocols.

The accelerometer 208, processor 218, sensors 216 and additional sensors 210 shown in FIG. 2 may be in wired or wireless communication with processing device 204. Display device 206 may also be in wired or wireless communication with processing device 204.

Figure 3:
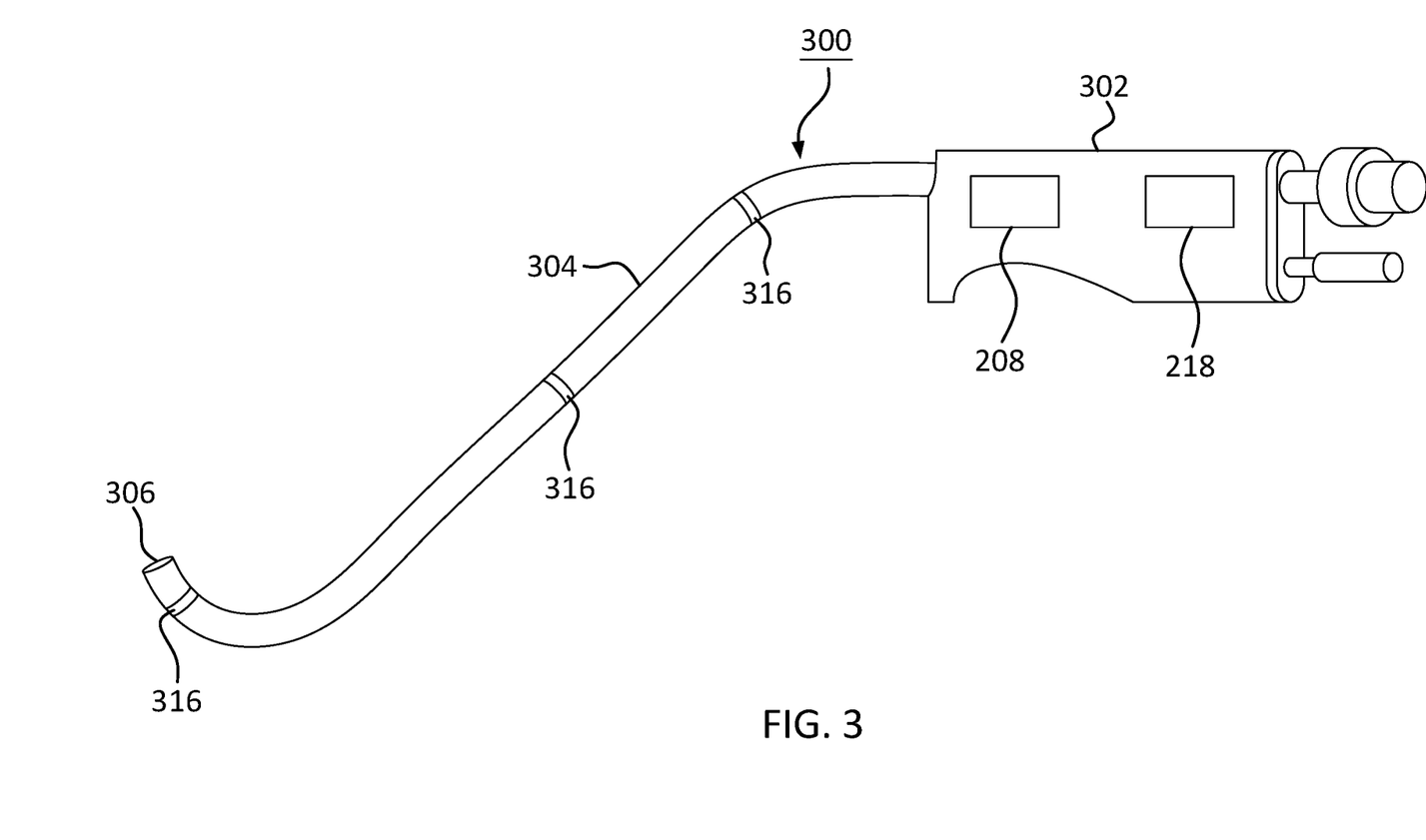
FIG. 3 is an illustration of an example wireless tool for use with embodiments described herein.

FIG. 3 is an illustration of an example wireless tool 300 for use with embodiments described herein. As shown in FIG. 3, tool 300 includes accelerometer 208 and processor 218. Wireless tool 300 includes a handle portion 302 and a probe portion 304. Probe portion 304 includes a tip 306 and sensors 316 disposed at different locations on the probe portion 304. As shown in FIG. 3, the accelerometer 208 and processor 218 is disposed at the handle portion 302 of the wireless tool 300. The size and shape of tool 300 shown in FIG. 3 is merely exemplary. In addition, the location of each component (e.g., sensors 216, accelerometer 208 and processor 218) shown in FIG. 3 is also exemplary.

The handle portion 302 is configured to be held by medical personnel for maneuvering the tool in 3-D space. The probe portion 304 is configured to be inserted into a patient during a medical procedure. As shown in FIG. 3, the handle portion 302 is attached to the probe portion 304. The sensors 316 are, for example, used to determine the location of the tool 300 and may include an inductor (not shown) and resistors (not shown) for transmitting signals (e.g. voltage) to a processor (e.g., processor 214 in FIG. 2) remote from the tool 300. The number of sensors 316 shown in FIG. 3 is by way of example. Embodiments include tools having any number of sensors, including one sensor, disposed at any number of tool locations.

The accelerometer 208, processor 218 and sensors 316 may be in wired or wireless communication with a processing device remote from the tool 300, such as processing device 204 shown in FIG. 2.

Figure 4:
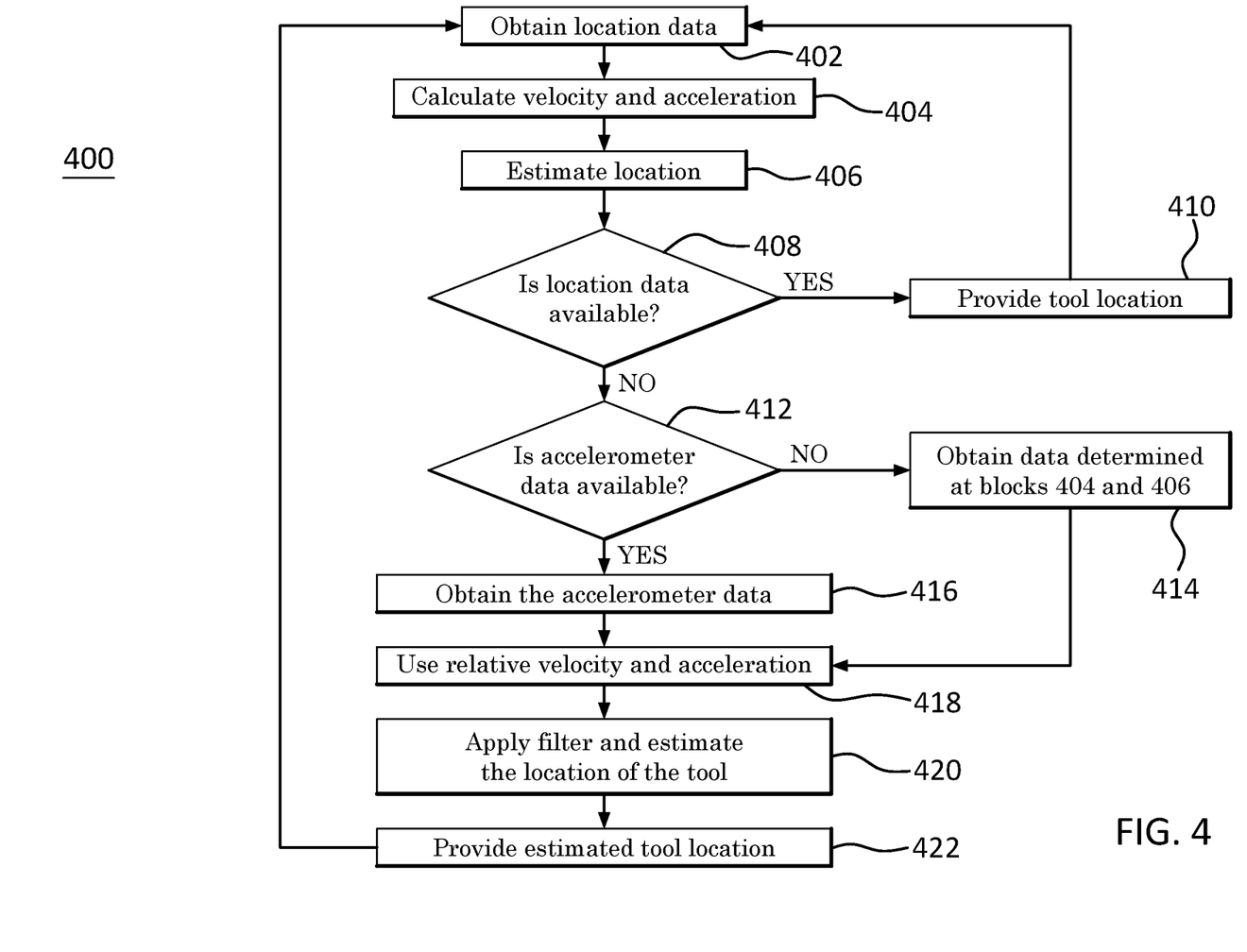
FIG. 4 is a flow diagram illustrating an example method of locating the tool in 3-D space according to an embodiment.

FIG. 4 is a flow diagram illustrating an example method 400 of locating the tool in 3-D space. As shown in block 402, the method 400 includes obtaining location data which corresponds to a location of a tool (e.g., tool 202) in 3D space over time. The location data may be obtained at the tool using one or more sensors (e.g. magnetic field location sensor 38 shown in FIG. 1, or sensors 216 shown in FIG. 2) disposed at the tool. The location data includes, for example, locations (e.g., points, coordinates) in the 3-D space, the strength of the magnetic data, times at which data is acquired (e.g., time stamps), and any other information indicating a location of the tool in the 3D space over time.

As shown in FIG. 4, the method 400 includes calculating the velocity and the acceleration of the tool, at block 404, and estimating the location of the tool, at block 406. The velocity and acceleration may be calculated at the tool or remote from the tool. In addition, the location of the tool may be estimated at the tool or remote from the tool.

For example, in one embodiment, the location data, obtained at the tool, may be transmitted from the tool and the velocity and the acceleration of the tool may be calculated remote from the tool (e.g., via processor 214) using the received location data. The location of the tool may then be estimated remote from the tool (e.g., via processor 214) from the calculated velocity and the acceleration. In another embodiment, the velocity and the acceleration of the tool may be calculated at the tool (e.g., via processor 218) using the obtained location data. The calculated velocity and acceleration may then be transmitted from the tool and the location of the tool may be estimated remote from the tool (e.g., via processor 214) from the calculated velocity and the acceleration calculated at the tool. In yet another embodiment, the velocity and the acceleration of the tool may be calculated at the tool and the location of the tool may be estimated at the tool. The estimated location of the tool may then be provided remote from the tool to be displayed.

In an example embodiment, the velocity of the tool is calculated using a change in location and a change in time. For example, assume that "x" is a previously acquired position of a tool acquired from block 402. A first velocity $V_1$ may be calculated using the Equation 1:

$$V_1 = (x_3 - x_2)/dt \qquad \text{(Equation 1)}$$

A second velocity, $V_2$ may be calculated using Equation 2:

$$V_2 = (x_2 - x_1)/dt \qquad \text{(Equation 2)}$$

where, "$x_1$," "$x_2$," and "$x_3$" are previously acquired positions of the tool at different times based on the location data obtained at block 402, and dt is the change in time between when two positions of the tool were acquired.

The acceleration may then be calculated (e.g., via processor 218 or 214) using two previously calculated velocities (e.g., $V_1$ and $V_2$) of the tool. For example, an acceleration "a" of the tool may be calculated using Equation 3:

$$a = (V_2 - V_1)/dt \qquad \text{(Equation 3)}$$

The calculated velocity and acceleration of the tool may then be used to estimate a location of the tool, at block 406. For example, the estimated location of the tool may be calculated using the sum of a previous location, a calculated velocity and a calculated acceleration, such as Equation 4:

$$x = x_0 + V_0 t + a_0((t^*t)/2) \qquad \text{(Equation 4)}$$

The equations described above, used to calculate the velocity and acceleration and estimate the location, are merely used as an example.

The location data, obtained via the magnetic fields, is continually obtained over time such that location data, corresponding to a plurality of locations of the tool at different times, is obtained. The velocity and acceleration of the tool are also continually calculated for locations over time. As shown at block 406, estimated location data is determined based on the continually calculated velocity and acceleration. For example, blocks 402-406 may be repeated, at equal intervals (e.g., 5 millisecond intervals), to continually estimate the location of the tool at the different locations over time. Each of blocks 402-406 may be repeated together (i.e., at the same equal intervals) or separate and independent from each other (i.e., at different intervals). Blocks 402-406 may also be repeated at unequal intervals, or performed upon the occurrence of an event or upon request.

As shown at block 408 of FIG. 4, a determination is made as to whether location data (e.g., most recently obtained location data corresponding to the location of the tool), obtained from block 402, is available for processing (e.g., processing by processor 214 or 218). That is, a determination is made as to whether location data, obtained via the magnetic fields, is available. If the location data is determined to be available, the location data is provided (e.g., to a display, a display processor, speaker), for presentation at block 410 and the location of the tool is presented (e.g., visually displayed, aurally presented, or any other known method of presenting information) at the location indicated by the location data. After the location of the tool is provided at block 410, the method proceeds back to block 402.

Location data may be determined not to be available for a variety of reasons. For example, location data may not be available if location signals (e.g., signals from magnetic field location sensor 38) are not received, if location signals are not strong enough to obtain information or the location data is determined to be inaccurate.

If the location data is determined not to be available at block 408, an estimation of the tool's location is performed. As shown in block 412, a determination is made as to whether accelerometer data is available for processing (e.g., by processor 214 or 218). The accelerometer data may not be available for a variety of reasons. For example, the accelerometer data may not be available if the tool is not equipped with an accelerometer, if the signals are not received, strong enough to acquire information end accelerometer data, or the accelerometer data is determined to be inaccurate.

As shown at block 414, if it is determined that the accelerometer data is not available, the data calculated at block 404 (e.g., one or more calculated accelerations) and the estimated location data determined at block 406, is obtained (e.g., from the tool or from memory 212 or storage 220). The location of the tool estimated from the relative velocity and acceleration (i.e., time when one or more velocities and accelerations are calculated relative to the current estimation), is used at block 418 to estimate the location (e.g., the current location) of the tool. That is, in the example shown at FIG. 4, estimated location data of the tool is continually generated over time (e.g., at equal intervals) at block 406, based on the calculated velocity and acceleration of the tool at block 404, prior to determining whether the location data is available at block 408.

In another example, estimated location data of the tool is generated if it is determined that the location data is not available. In this example, the calculated velocity and acceleration is obtained at 414 and then the estimated location data is generated using the relative velocity and acceleration.

If the accelerometer data is determined to be available, the accelerometer data is obtained at block 416 and the relative acceleration data of the accelerometer data obtained from the accelerometer is used to estimate the location of the tool at block 418.

One or more previous velocity calculations performed in block 404 and one or more previous acceleration calculations, or accelerometer data, may be used to estimate the location of the tool. For example, more recently (e.g., most recent) obtained velocity data, acceleration data and accelerometer data is used to estimate the location of the tool. In addition to or alternative to the more recently obtained data, other data prior to the more recently obtained data may be used, for example, because the more recent data may be inaccurate, include errors in calculation or may not be processable (e.g., signal including the data is not strong enough or signals are not received).

As shown in block 420, a filter may be applied to the relative velocity and acceleration, obtained at block 418, to estimate the location of the tool. In one exemplary embodiment, a Kalman filter is used. For example, Equation 5 may be used to estimate the location of the tool:

$$Pk = P(k-1) + dtV(k-1) + 1/2 * adt^2 \quad \text{(Equation 5)}$$

where, the location of the tool at a relative time "Pk" is based on the location at a prior relative time "k−1", the velocity at a relative time "(V(k−1))" and a change in time of the acceleration of the tool "adt."

As shown at block 422, the estimated location data, corresponding to an estimated location of the tool, is provided (e.g., to a display, a display processor, speaker) for presentation and the location of the tool is presented (e.g., visually displayed, aurally presented, or any other known method of presenting information) at the location indicated by the location data. After the estimated location of the tool is provided at block 422, the method proceeds back to block 402.

Any of the functions and methods described herein can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A method for locating a medical tool in a three dimensional (3D) space within a heart during a surgical procedure using an electromagnetic navigation system, the method comprising:

receiving transmitting signals from one or more sensors of the medical tool, the one or more sensors comprising at least a magnetic field location sensor disposed at a tip of the medical tool, the magnetic field location sensor provides an amplitude and a phase of magnetic fields within the heart within the transmitting signals, the magnetic fields being generated by one or more magnetic field generators external to the heart, and the amplitude and the phase indicating a strength of the magnetic fields being detected by the magnetic field location sensor;

determining whether location data, corresponding to a location of the medical tool, is available;

if the location data is available within the transmitting signals:
controlling a display of the location of the medical tool based on the location data; and
providing anatomical information comprising maps of the heart in the display based on the location data; and if the location data is not available within the transmitting signals:
determining an estimated location of the medical tool based on the transmitting signals comprising a velocity of the medical tool and an acceleration of the medical tool in accordance with the strength of the magnetic fields;
continually generating estimated location data corresponding to the estimated location of the medical tool over time at equal intervals based on the velocity and the acceleration of the medical tool;
controlling the display of the location of the medical tool based on the estimated location data; and
providing in the display for presentation the estimated location data, the anatomical information comprising the maps of the heart based on the estimated location data, and the location of the medical tool.

2. The method of claim 1, further comprising:
receiving an indication of the location of the medical tool; and
generating the indication of the location of the medical tool.

3. The method of claim 1, wherein if the location data is not available,
determining whether accelerometer data, which indicates the acceleration of the medical tool, is available; and
if the accelerometer data is available, determining the estimated location of the medical tool based on the accelerometer data.

4. The method of claim 1, further comprising:
calculating the velocity of the medical tool and the acceleration of the medical tool for a plurality of locations over time, and
determining whether accelerometer data, which indicates the acceleration of the medical tool, is available; and
if the accelerometer data is not available, determining the estimated location of the medical tool using one or more previous velocity calculations and one or more previous acceleration calculations of the medical tool.

5. The method of claim 4, wherein:
the one or more previous velocity calculations comprise calculating the velocity of the medical tool based on a change in location and a change in time; and
the one or more previous acceleration calculations comprise calculating the acceleration based on a change in the velocity and a change in time.

6. The method of claim 1, wherein the estimated location of the medical tool is determined remote from the medical tool.

7. The method of claim 1, wherein the estimated location of the medical tool is determined local to the medical tool.

8. The method of claim 1, wherein if the location data is not available:
filtering, via a Kalman filter, the estimated location data to provide filtered estimated location data; and
providing the filtered estimated location data for presenting the estimated location of the medical tool.

9. The method of claim 1, wherein the magnetic field location sensor comprises one or more receiving coils oriented along different axes and the one or more magnetic field generators comprise one or more emitter coils.

10. The method of claim 1, wherein the location data include points in 3-D space, the strength of the magnetic fields, and a time stamp.

11. The method of claim 1, wherein the estimated location data is obtained from a relative velocity and acceleration based on a time when one or more velocities and accelerations are calculated relative to a current estimation.

12. The method of claim 1, wherein the method further comprises:
calculating the velocity of the medical tool includes using location and time changes to calculate first and second velocities;
calculating the acceleration of the medical tool using the first and second velocities; and
determining the estimated location of the medical tool is based on calculating using a sum of a previous location, the velocity, and the acceleration.

13. The method of claim 1, wherein the velocity and acceleration of the medical tool are calculated for a plurality of locations over time, and wherein the equal intervals comprise five (5) millisecond intervals.

14. An electromagnetic navigation system for locating a medical tool in a three dimensional (3D) space within a heart during a surgical procedure, the electromagnetic navigation system comprising:
a memory configured to store data; and
a processor, in communication with the memory, configured to:
receive transmitting signals from one or more sensors of the medical tool, the one or more sensors comprising at least a magnetic field location sensor disposed at a tip of the medical tool, the magnetic field location sensor provides an amplitude and a phase of magnetic fields within the heart within the transmitting signals, the magnetic fields being generated by one or more magnetic field generators external to the heart, and the amplitude and the phase indicating a strength of the magnetic fields being detected by the magnetic field location sensor;
determine whether location data, corresponding to a location of the medical tool, is available;
if the location data is available within the transmitting signals;
control a display of the location of the medical tool based on the location data; and
provide anatomical information comprising maps of the heart in the display based on the location data; and
if the location data is not available within the transmitting signals:
determine an estimated location of the medical tool based on the transmitting signals comprising a velocity of the medical tool and an acceleration of the medical tool in accordance with the strength of the magnetic fields;
continually generate estimated location data corresponding to the estimated location of the medical tool over time at equal intervals based on the velocity and the acceleration of the medical tool;
control the display of the location of the medical tool based on the estimated location data; and
provide in the display for presentation the estimated location data, the anatomical information comprising the maps of the heart based on the estimated location data, and the location of the medical tool.

15. The electromagnetic navigation system of claim 14, wherein the processor is further configured to:
receive electrical signals indicating a plurality of locations of the medical tool over time; and
generate the location data based on the electrical signals.

16. The electromagnetic navigation system of claim 14, wherein if the location data is not available, the processor is further configured to determine whether accelerometer data, which indicates the acceleration of the medical tool, is available; and
if the accelerometer data is available, the processor is further configured to determine the estimated location of the medical tool based on the velocity of the medical tool and the accelerometer data.

17. The electromagnetic navigation system of claim 14, wherein the velocity and acceleration of the medical tool are calculated, over time, for each of a plurality of locations, and
the processor is further configured to determine whether accelerometer data, which indicates the acceleration of the medical tool, is available; and
if the accelerometer data is not available, the processor is further configured to determine the estimated location of the medical tool by using one or more previous velocity calculations and one or more previous acceleration calculations of the medical tool.

18. The electromagnetic navigation system of claim 14, wherein if the location data is not available:
filtering, via a Kalman filter, the estimated location data to provide filtered estimated location data; and
providing the filtered estimated location data for presenting the estimated location of the medical tool.

19. A non-transitory computer readable medium having instructions locating a medical tool in a three dimensional (3D) space within a heart during a surgical procedure using an electromagnetic navigation system, the instructions executable by a computer of the electromagnetic navigation system to cause the electromagnetic navigation system to perform:
receiving transmitting signals from one or more sensors of the medical tool, the one or more sensors comprising at least a magnetic field location sensor disposed at a tip of the medical tool, the magnetic field location sensor provides an amplitude and a phase of magnetic fields within the heart within the transmitting signals, the magnetic fields being generated by one or more magnetic field generators external to the heart, and the amplitude and the phase indicating a strength of the magnetic fields being detected by the magnetic field location sensor;
receiving electrical signals indicating the location of the medical tool;
generating location data based on the electrical signals;
determining whether the location data, corresponding to a location of the medical tool, is available and whether accelerometer data, which indicates an acceleration of the medical tool, is available;
if the location data is available within the transmitting signals:
controlling a display of the location of the medical tool based on the location data; and
providing anatomical information comprising maps of the heart in the display based on the location data; and
if the location data is not available within the transmitting signals:
continually determining estimated location data over time at equal intervals, corresponding to an estimated location of the medical tool based on the transmitting signals comprising a velocity of the medical tool and the acceleration of the medical tool in accordance with the strength of the magnetic fields, the velocity and acceleration of the medical tool are calculated for a plurality of locations over time;
controlling the display of the location of the medical tool based on the estimated location data; and
providing in the display for presentation the estimated location data, the anatomical information comprising the maps of the heart based on the estimated location data, and the location of the medical tool.

20. The non-transitory computer readable medium according to claim 19, wherein the instructions are executable to cause the electromagnetic navigation system to perform:
if the accelerometer data is available, determining the estimated location of the medical tool based on the velocity of the medical tool and the accelerometer data; and
if the accelerometer data is not available, determining the estimated location of the medical tool further comprises determining a current estimated location of the medical tool using one or more previous velocity and acceleration calculations of the medical tool at one or more previous locations.

* * * * *

UNITED STATES PATENT AND TRADEMARK OFFICE
CERTIFICATE OF CORRECTION

PATENT NO. : 11,646,113 B2
APPLICATION NO. : 15/935777
DATED : May 9, 2023
INVENTOR(S) : Vadim Gliner et al.

It is certified that error appears in the above-identified patent and that said Letters Patent is hereby corrected as shown below:

On the Title Page

On Page 2, in Item (56), under "OTHER PUBLICATIONS", in Column 2, Line 1, delete ""u-blox" and insert -- "u-blox' --, therefor.

In the Specification

In Column 2, Line 27-28, delete "(Institute of Electrical Engineers" and insert -- Institute of Electrical and Electronics Engineers --, therefor.

In Column 2, Line 28, delete "IrDA (infrared data)" and insert -- Infrared Data Association (IrDA) --, therefor.

In Column 5, Line 48, delete "patient" and insert -- patient's --, therefor.

In Column 5, Line 65, delete "sp ace." and insert -- space. --, therefor.

In the Claims

In Column 11, Line 9, in Claim 3, delete "available," and insert -- available: --, therefor.

In Column 12, Line 22, in Claim 14, delete "signals;" and insert -- signals: --, therefor.

Signed and Sealed this
Nineteenth Day of September, 2023

Katherine Kelly Vidal
*Director of the United States Patent and Trademark Office*